US008552184B2

(12) United States Patent
Reaume et al.

(10) Patent No.: US 8,552,184 B2
(45) Date of Patent: Oct. 8, 2013

(54) COMPOUNDS AND METHODS FOR TREATING DISORDERS RELATED TO GLUCOSE METABOLISM

(75) Inventors: Andrew G. Reaume, Exton, PA (US); Michael S. Saporito, Exton, PA (US); Alexander R. Ochman, Exton, PA (US); Christopher K. Lipinski, Waterford, CT (US)

(73) Assignee: Melior Pharmaceuticals I, Inc., Exton, PA (US)

(*) Notice: Subject to any disclaimer, the term of this patent is extended or adjusted under 35 U.S.C. 154(b) by 421 days.

(21) Appl. No.: 12/495,857

(22) Filed: Jul. 1, 2009

(65) Prior Publication Data

US 2010/0004273 A1 Jan. 7, 2010

Related U.S. Application Data

(60) Provisional application No. 61/078,193, filed on Jul. 3, 2008.

(51) Int. Cl.
*C07D 239/06* (2006.01)
*C07D 239/02* (2006.01)
*A61K 31/505* (2006.01)

(52) U.S. Cl.
USPC ............................ 544/302; 544/314; 514/274

(58) Field of Classification Search
USPC .................................. 514/274; 544/302, 314
See application file for complete search history.

(56) References Cited

U.S. PATENT DOCUMENTS

| | | | |
|---|---|---|---|
| 3,174,901 | A | 3/1965 | Sterne |
| 3,922,345 | A | 11/1975 | Lipinski et al. |
| 4,080,454 | A | 3/1978 | Lipinski |
| 4,824,851 | A | 4/1989 | Takaya et al. |
| 5,476,855 | A | 12/1995 | Kouni et al. |
| 5,698,155 | A | 12/1997 | Grosswald et al. |
| 5,721,114 | A | 2/1998 | Abrahamsen et al. |
| 5,721,241 | A * | 2/1998 | el Kouni et al. ............. 514/269 |
| 6,004,925 | A | 12/1999 | Dasseux et al. |
| 6,037,323 | A | 3/2000 | Dasseux et al. |
| 6,410,255 | B1 | 6/2002 | Pollok et al. |
| 7,776,870 | B2 | 8/2010 | Reaume et al. |
| 8,343,985 | B2 | 1/2013 | Reaume et al. |
| 2002/0151497 | A1 | 10/2002 | Ben-Sasson |
| 2005/0009817 | A1 | 1/2005 | Savoy et al. |
| 2005/0208054 | A1 | 9/2005 | Czech et al. |
| 2006/0024365 | A1 | 2/2006 | Vaya et al. |
| 2006/0035302 | A1 | 2/2006 | Lee |
| 2006/0252777 | A1 | 11/2006 | Kim et al. |
| 2007/0049609 | A1 | 3/2007 | Broka et al. |
| 2007/0093516 | A1 | 4/2007 | Reaume et al. |
| 2007/0185070 | A1 | 8/2007 | Pershadsingh |
| 2010/0278804 | A1 | 11/2010 | Reaume et al. |

FOREIGN PATENT DOCUMENTS

| | | |
|---|---|---|
| CN | 1395560 A | 2/2003 |
| EP | 1541694 A1 | 6/2005 |
| GB | 1377308 | 12/1974 |
| JP | 2007037546 | 2/2007 |
| WO | 94/01414 A1 | 1/1994 |
| WO | 01/51463 A1 | 7/2001 |
| WO | 02/068394 A1 | 9/2002 |
| WO | 94/01414 A1 | 9/2002 |
| WO | 02/095058 | 11/2002 |
| WO | 2007/024863 A2 | 3/2007 |
| WO | 2009015133 | 1/2009 |

OTHER PUBLICATIONS

Muller, G., et al., Interaction of phosphatidylinositolglycan(-peptides) with plasma membrane lipid rafts triggers insulin-mimetic signaling in rat adipocytes, Archives of Biochemistry and Biophysics, 2002;408:7-16.

Masuda, H., et al., Peptic Ulcer in Diabetes Millitus, Gastroenterologia Japonica, 1976;11(1):1-4.

Briggs, S.D. et al., Affinity of Src Family Kinase SH3 Domains for HIV Nef In Vitro Does Not Predict Kinase Activation by Nef In Vivo, Biochemistry, 2000;39:489-495.

Ishikawa, H. et al., "Requirements of src family kinase activity associated with CD45 for myeloma cell proliferation by interleukin-6." Blood 99: 2172-2178 (2002).

Reaven, Role of insulin resistance in human disease (syndrome X): an expanded definition, Annu Rev Med (1993) 44:121-131.

Blasioli, J. et al., Lyn/CD22/SHP-1 and their importance in autoimmunity, Curr. Dir. Autoimmun. 5: 151-160 (2002).

Langer, R., New methods of drug delivery, Science vol. 249, Issue 4976, 1527-1533 (1990).

Treat et al., Liposomes in the Therapy of Infectious Disease and Cancer, Lopez-Berestein and Fidler (eds.), Liss, New York, pp. 353-365 (1989).

Lopez-Berestein, G., Treatment of Systemic Fungal Infections with Liposomal-Amphotericin B, 1989 ibid., pp. 317-327.

Sefton, Michael V., Implantable Pumps, CRC Crit. Ref. Biomed. Eng., 1987;14(3):201-40.

Buchwald, Henry, et al., Long-tern, continuous intravenous heparin administration by an implantable infusion pump in ambulatory patients with recurrent venous thrombosis, Surgery, Oct. 1987;88(4):507-16.

Langer and Wise (eds.) "Medical Applications of Controlled Release," CRC Pres., Boca Raton, Fla. (1974).

Smolen and Ball (eds.), "Controlled Drug Bioavailability, Drug Product Design and Performance," Wiley, New York (1984).

(Continued)

*Primary Examiner* — James O Wilson
*Assistant Examiner* — Ebenezer O Sackey
(74) *Attorney, Agent, or Firm* — Pepper Hamilton, LLP

(57) ABSTRACT

The present invention relates to compounds and pharmaceutically acceptable salts thereof, and compositions comprising the same, that are useful in modulating lyn kinase activity, treating obesity, type II diabetes, metabolic syndrome, and in reducing blood glucose level, weight gain, or fat depot level, or treating a disease or condition associated with the same.

20 Claims, No Drawings

(56) References Cited

OTHER PUBLICATIONS

Langer, Robert and Peppas, Nikolaos, Chemical and Physical Structure of Polymers as Carriers for Controlled Release of Bioactive Agents: A Review, JMS-Rev. Macromol. Chem. Phys., 1983; 23(1):61-126.
Levy, R. J. et al., Inhibition of calcification of bioprosthetic heart valves by local controlled-release diphosphonate, Science vol. 228, Issue 4696, pp. 190-192 (1985).
During, Matthew J., et al., Controlled Release of Dopamine from a Polymeric Brain Implant: In Vivo Characterization, Annals of Neurology, Apr. 1989; 25(4):351-56.
Howard, Matthew A., III, et al., Intracerebral drug delivery in rats with lesion-induced memory deficits, J. Neurosurg., Jul. 1989; 71:105-112.
Goodson, "Medical Applications Controlled Release" supra [J. Neurosurg.], vol. 2, pp. 115-138 (1984).
Lipinski, C. A. et al., Bronchodilator and Antiulcer Phenoxypyrimidiones, J. Med. Chem. 1980; 23:1026-1031.
Z-Lyte Kinase Assay Kits, Invitrogen website http://www.invitrogen.com.
International Search Report dated Jul. 25, 2008 for PCT/US2008/054361.
International Search Report dated Feb. 26, 2007 for PCT1US2006/032788.
International Search Report dated Oct. 6, 2008 for PCT/US2008/070739.
International Search Report dated Sep. 1, 2009 for PCT/US2009/049509.
Non-Final Office Action for co-pending U.S. Appl. No. 11/507,652 dated Sep. 7, 2007.
Final Office Action for co-pending U.S. Appl. No. 11/507,652 dated Mar. 12, 2008.
Non-Final Office Action for co-pending U.S. Appl. No. 11/507,652 dated Sep. 10, 2008.
Non-Final Office Action for co-pending U.S. Appl. No. 11/507,652 dated march 20, 2009.
Notice of Allowance for co-pending U.S. Appl. No. 11/507,652 dated Apr. 9, 2010.
Johnson, S. A. et al., Phosphorylated immunoreceptor signaling motifs (ITAMs) exhibit unique abilities to bind and activate Lyn and Syk tyrosine kinases, J Immunol. Nov. 15, 1995;155(10):4596-603.
Anonymous, Src Kinase, Dec. 2006 1:1-3, URL:http://www.cellsignal.com/pdf/7775.pdf.
Wesch, H., et al., High throughput screening for protein kinase inhibitors, Comb Chem High Throughput Screen. Mar. 2005;8(2):181-95.
Non-Final Office Action for co-pending U.S. Appl. No. 11/507,652 dated Dec. 11, 2009.
Non-Final Office Action for co-pending U.S. Appl. No. 12/837,067 dated Nov. 16, 2011.
International Search Report dated Sep. 1, 2009.
Non-final Office Action dated Jun. 27, 2012, in co-pending U.S. Appl. No. 12/527,801.
Summy, J. M., et al., AP23846, a novel and highly potent Src family kinase inhibitor, reduces vascular endothelial growth factor and interleukin-8 expression in human solid tumor cell lines and abrogates downstream angiogenic processes, Mol Cancer Ther. Dec. 2005;4(12):1900-11.
Bozulic, L.C., et al., The influence of Lyn kinase on Na,K-ATPase in porcine lens epithelium, Am J Physiol Cell Physiol. Jan. 2004;286(1):C90-6.
Advisory Action dated Apr. 13, 2012 received in copending U.S. Appl. No. 12/837,067.
Final Office Action dated Jan. 19, 2012 in co-pending U.S. Appl. No. 12/837,067.
Notice of Allowance dated Aug. 31, 2012 in co-pending U.S. Appl. No. 12/837,067.
Non-Final Office Action dated May 28, 2013 received in copending U.S. Appl. No. 13/690,548.
Non-Final Office Action dated Apr. 11, 2013 received in copending U.S. Appl. No. 13/700,191.

* cited by examiner

COMPOUNDS AND METHODS FOR TREATING DISORDERS RELATED TO GLUCOSE METABOLISM

CROSS-REFERENCE TO RELATED APPLICATIONS

This application claims priority to U.S. provisional application Ser. No. 61/078,193 filed Jul. 3, 2008, which is incorporated herein by reference in its entirety.

FIELD OF THE INVENTION

The present invention provides compounds and pharmaceutically acceptable salts thereof, and compositions comprising the same, that are useful in modulating lyn kinase activity, treating obesity, type II diabetes, and/or metabolic syndrome, and in reducing blood glucose level, weight gain, or fat depot level, and treating a disease or condition associated with therewith.

BACKGROUND OF THE INVENTION

Lyn kinase is a member of the src family of non-receptor protein tyrosine kinases that is predominantly expressed in B-lymphoid and myeloid cells (see, Briggs et al., Biochemistry, 2000, 39, 489-495). Lyn participates in signal transduction from cell surface receptors that lack intrinsic tyrosine kinase activity. Activation of the lyn kinase activity is necessary for proliferation of CD45+ myeloma cells stimulated by IL-6 (see, Ishikawa et al., Blood, 2002, 99, 2172-2178). Association of lyn and fyn with the proline-rich domain of glycoprotein VI regulates intracellular signaling (see, Suzuki-Inoue et al., J. Biol. Chem., 2002, 277, 21561-21566). The lyn/CD22/SHP-1 pathway is important in autoimmunity (see, Blasioli et al., Curr. Dir. Autoimmun., 2002, 5, 151-160).

Obesity, hyperlipidemia, and diabetes have been shown to play a causal role in various disorders including, for example, atherosclerotic cardiovascular diseases, which currently account for a considerable proportion of morbidity in Western society. One human disorder, termed "Syndrome X" or "Metabolic Syndrome," is manifested by defective glucose metabolism (e.g., insulin resistance), elevated blood pressure (i.e., hypertension), and a blood lipid imbalance (i.e., dyslipidemia) (see Reaven, Annu. Rev. Med., 1993, 44, 121-131).

There is a need to discover compounds that have the ability to modulate lyn kinase or manage elevated glucose levels that may have a usefulness in regulating lipid, lipoprotein, insulin and/or glucose levels in the blood. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by glucose metabolism and/or elevated glucose levels.

SUMMARY OF THE INVENTION

The present invention provides compounds that may be useful in modulating the activity of lyn kinase. In particular, the compounds that may be useful in modulating the activity of lyn kinase include, but are not limited to, the compounds of Formulas I, Ia, Ib, II, III, and IV. In an illustrative embodiment, the compounds may up-regulate or increase the activity and/or expression of lyn kinase. Thus, the compounds of Formulas I, Ia, Ib, II, III, and IV may act as activators or agonists of lyn kinase. The compounds of Formulas I, Ia, Ib, II, III, and IV may direct modulation of lyn kinase in the insulin receptor pathway (i.e., lyn activation has insulin receptor activation-like activity).

The present invention also provides methods of treating or preventing a disease or disorder including, but not limited to, cardiovascular disease, dyslipidemia, reducing fat depot levels, reducing weight gain, reducing blood glucose levels, dyslipoproteinemia, a disorder of glucose metabolism (i.e., elevated blood glucose levels), metabolic syndrome (i.e., Syndrome X), a PPAR-associated disorder, septicemia, a thrombotic disorder, type II diabetes, cancer, obesity, pancreatitis, hypertension, a renal disease, inflammation, and impotence comprising administering to a subject, such as a mammal, a therapeutically or prophylactically effective amount of a compound of Formula I, Ia, Ib, II, III, or IV or composition or formulation comprising a compound of Formula I, Ia, Ib, II, III, or IV. In some embodiments, the mammal will be in need thereof of such treatment or prophylaxis.

In one embodiment, the composition comprising a compound of Formula I, Ia, Ib, II, III, or IV is for use in treating or preventing metabolic syndrome or Syndrome X or the treatment of disorders associated with these syndromes including, but not limited to, obesity, prediabetes, and type II diabetes as well as complications of obesity and diabetes. Complications of obesity include, but are not limited to, hypercholesterolemia, hypertension, and coronary heart disease. Complications of diabetes include, but are not limited to, diabetic neuropathy, diabetic retinopathy, erectile dysfunction, and kidney disease.

As described herein, the compositions that are useful in the methods described herein encompass compounds of Formulas I, Ia, Ib, II, III, and IV.

In some embodiments, the compound is of Formula I

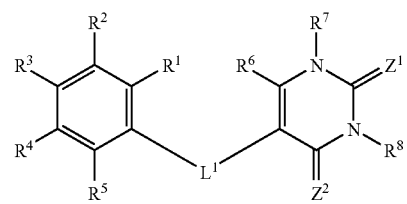

wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{12}$, $OC(O)R^{b2}$, $OC(O)NR^{c2}R^{d2}$, $NR^{c2}R^{d2}$, $NR^{c2}C(O)^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^2C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{c2}$, $NR^{c2}C(O)R^{b2}$, $NR^{c2}C(O)NR^{c2}R^{c2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or two adjacent groups of $R^1$, $R^2$, $R^3$, $R^4$, and $R^5$ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^6$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^7$ is H, $C_{1-6}$alkyl, $C_{1-6}$haloalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^8$ is H, $C_{1-6}$alkyl, $C_{1-6}$haloalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

or a pharmaceutically acceptable salt thereof. In some embodiments, the compound is not 5-m-methylphenoxyuracil or a pharmaceutically acceptable salt thereof.

In some embodiments, the compound of Formula I has Formula Ia:

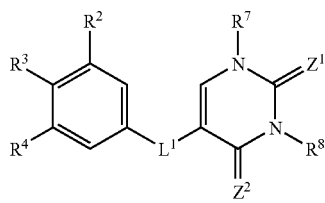

Ia wherein:

$R^2$, $R^3$, and $R^4$ are each, independently, H, halo, $C_{1-6}$alkyl, $C_{1-6}$hydroxyalkyl, or $C_{1-6}$haloalkyl;

$R^7$ is H, $C_{1-6}$alkyl, $C(O)R^{b1}$, $C(O)NR^{c1}R^{d1}$, or $C(O)OR^{a1}$;

$R^8$ is H, $C_{1-6}$alkyl, $C(O)R^{b1}$, $C(O)NR^{c1}R^{d1}$, or $C(O)OR^{a1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O or S;

$Z^2$ is O or S; and $L^1$ is O or S.

In some embodiments, the compound of Formula I has Formula Ib:

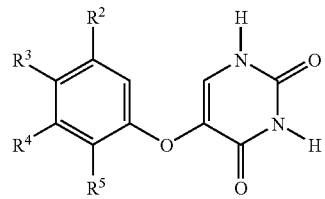

Ib wherein:

$R^2$, $R^3$, $R^4$, and $R^5$ are each, independently, H, F, Cl, $CH_3$, $SCH_3$, $OCH_3$, $C(CH_3)_3$, $CH(CH_3)_2$, or $C_2H_5$.

In some embodiments, the compound is of Formula II, Formula III, or Formula IV:

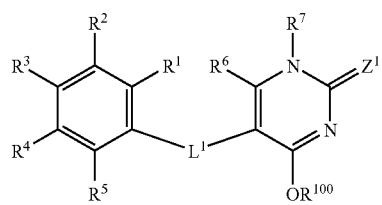

II

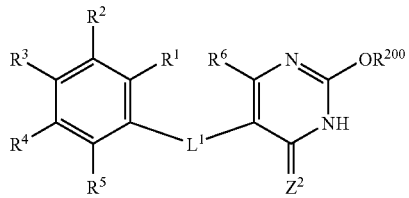

III

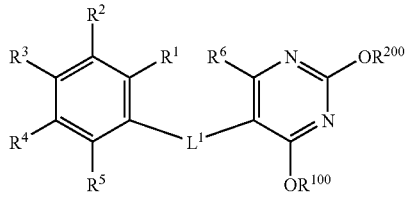

IV wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^4$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{c1}$R$^{d1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^5$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

or two adjacent groups of R$^1$, R$^2$, R$^3$, R$^4$, and R$^5$ can link to form a fused cycloalkyl or fused heterocycloalkyl group, each optionally substituted by 1, 2, or 3 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^6$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^7$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$;

R$^{a1}$, R$^{b1}$, R$^{c1}$, and R$^{d1}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

R$^{a2}$, R$^{b2}$, R$^{c2}$, and R$^{d2}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

or R$^{c2}$ and R$^{d2}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

Z$^1$ is O, S, or NR$^9$;

R$^9$ is H, OH, C$_{1-6}$alkoxy, C$_{1-6}$haloalkyl, C$_{1-6}$hydroxyalkyl, aryloxy, heteroaryloxy, CN, or NO$_2$;

Z$^2$ is O, S, or NR$^{10}$;

R$^{10}$ is H, OH, C$_{1-6}$alkoxy, C$_{1-6}$haloalkyl, C$_{1-6}$hydroxyalkyl, aryloxy, heteroaryloxy, CN, or NO$_2$;

L$^1$ is O, S, or NR$^{11}$; and

R$^{11}$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$;

R$^{100}$ is a hydroxyl protecting group, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, heterocycloalkyl, aryl, heteroaryl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, S(O)$_2$NR$^{c1}$R$^{d1}$, S(O)$_2$R$^{e1}$, P(O)OR$^{f1}$OR$^{g1}$, or Si(R$^{h1}$)$_3$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4 or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

each $R^{f1}$ is, independently, H, $C_{1-6}$alkyl, $C_{1-6}$haloalkyl, $C_{1-6}$hydroxyalkyl, $C_{2-6}$alkenyl, $(C_{1-6}$alkoxy)-$C_{1-6}$alkyl, $C_{2-6}$alkynyl, aryl, cycloalkyl, heteroaryl, heterocycloalkyl, arylalkyl, cycloalkylalkyl, heteroarylalkyl, or heterocycloalkylalkyl;

each $R^{g1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, or heterocycloalkyl; and each $R^{h1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

or a pharmaceutically acceptable salt thereof. In some embodiments, for a compound of Formula II, when $Z^1$ is O or S, $R^7$ is H, and $L^1$ is O, S, or $NR^{11}$, wherein $R^{11}$ is H or $C_{1-6}$alkyl, then $R^{100}$ is not $C_{1-6}$alkyl or aryl.

The present invention also provides compounds (as disclosed in any of the embodiments described herein) for use in modulating lyn kinase activity, treating obesity, type II diabetes, and/or metabolic syndrome, and/or in reducing blood glucose level, weight gain, or fat depot level.

The present invention also provides compounds (as disclosed in any of the embodiments described herein) for use preparation of a medicament for modulating lyn kinase activity, treating obesity, type II diabetes, and/or metabolic syndrome, and/or for reducing blood glucose level, weight gain, or fat depot level.

DETAILED DESCRIPTION OF EMBODIMENTS

As used herein and unless otherwise indicated, the phrase "altering lipid metabolism" indicates an observable (i.e., measurable) change in at least one aspect of lipid metabolism including, but not limited to, total blood lipid content, blood HDL cholesterol, blood LDL cholesterol, blood VLDL cholesterol, blood triglyceride, blood Lp(a), blood apo A-I, blood apo E or blood non-esterified fatty acids.

As used herein and unless otherwise indicated, the phrase "altering glucose metabolism" indicates an observable (i.e., measurable) change in at least one aspect of glucose metabolism including, but not limited to, total blood glucose content, blood insulin, the blood insulin to blood glucose ratio, insulin sensitivity, or oxygen consumption.

As used herein and unless otherwise indicated, the term "alkoxy group" means an —O-alkyl group, wherein alkyl is as defined herein. An alkoxy group can be unsubstituted or substituted with one or two suitable substituents. The alkyl chain of an alkyloxy group is from 1 to 6 carbon atoms in length, referred to herein, for example, as "$(C_1-C_6)$alkoxy."

As used herein and unless otherwise indicated, the term "alkyl" or "alkyl group" means a saturated, monovalent unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to, $(C_2-C_6)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein and unless otherwise indicated, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. The aryl group can be a monocyclic ring, wherein the ring comprises 6 carbon atoms, referred to herein as "$(C_6)$aryl."

As used herein and unless otherwise indicated, the term "aryloxy group" means an —O-aryl group, wherein aryl is as defined herein. An aryloxy group can be unsubstituted or substituted with one or two suitable substituents. The aryl ring of an aryloxy group can be a monocyclic ring, wherein the ring comprises 6 carbon atoms, referred to herein as "$(C_6)$aryloxy."

As used herein and unless otherwise indicated, the term "benzyl" means —$CH_2$-phenyl.

As used herein and unless otherwise indicated, the term "carbonyl" group is a divalent group of the formula —C(O)—.

As used herein and unless otherwise indicated, the term "compounds of the invention" means, collectively, the compounds of formulas I, Ia, II, III, and/or IV and pharmaceutically acceptable salts thereof. These compounds are identified herein by their chemical structure and/or chemical name. Where a compound is referred to by both a chemical structure and a chemical name, and that chemical structure and chemical name conflict, the chemical structure is determinative of the compound's identity. The compounds of Formulas I, Ia, Ib, II, III, and/or IV may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of Formulas I, Ia, Ib, II, III, and/or IV, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein and unless otherwise indicated, the term "cycloalkyl group" means a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. The cycloalkyl group can be a monocyclic ring or bicyclic ring.

As used herein and unless otherwise indicated, the terms "diabetes" and "type II diabetes" are used interchangeably and include, but are not limited to, non-insulin dependent diabetes mellitus, diabetes insipidus, and are related to insulin resistance (i.e., lack of the ability of the body to respond to insulin appropriately) and is often accompanied by related complications including, for example, obesity and high cholesterol.

As used herein and unless otherwise indicated, the term "halogen" means fluorine, chlorine, bromine, or iodine. Correspondingly, the meaning of the terms "halo" and "Hal" encompass fluoro, chloro, bromo, and iodo. For example, suitable $C_{1-3}$haloalkyl or $C_{1-6}$haloalkyl groups include, but are not limited to, fluoro-$C_{1-3}$alkyl or fluoro-$C_{1-6}$alkyl groups.

As used herein and unless otherwise indicated, the term "heteroaryl group" means a monocyclic- or polycyclic aromatic ring comprising carbon atoms, hydrogen atoms, and one or more heteroatoms, such as 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, furyl, phenyl, isoxazolyl, and oxazolyl. A heteroaryl group can be unsubstituted or substituted with one or two suitable substituents. A heteroaryl group can be a monocyclic ring, wherein the ring comprises 2 to 5 carbon atoms and 1 to 3 heteroatoms, referred to herein as "$(C_2-C_5)$ heteroaryl."

As used herein and unless otherwise indicated, the term "heterocycloalkyl group" means a monocyclic or polycyclic ring comprising carbon and hydrogen atoms and at least one heteroatom, such as 1 to 3 heteroatoms, selected from nitrogen, oxygen, and sulfur, and having no unsaturation. Examples of heterocycloalkyl groups include, but are not limited to, pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. The heterocycloalkyl group can be a monocyclic or bicyclic ring, wherein the ring comprises from 3 to 6 carbon atoms and form 1 to 3 heteroatoms, referred to herein as $(C_1-C_6)$heterocycloalkyl.

As used herein and unless otherwise indicated, the term "heterocyclic radical" or "heterocyclic ring" means a heterocycloalkyl group or a heteroaryl group.

As used herein and unless otherwise indicated, the term "hydrocarbyl group" means a monovalent group selected from $(C_1-C_8)$alkyl, $(C_2-C_8)$alkenyl, and $(C_2-C_8)$alkynyl, optionally substituted with one or two suitable substituents. The hydrocarbon chain of a hydrocarbyl group can be from 1 to 6 carbon atoms in length, referred to herein as $(C_1-C_6)$ hydrocarbyl.

When administered to a mammal (e.g., to an animal for veterinary use or to a human for clinical use) the compounds of Formulas I, Ia, Ib, II, III, and/or IV are administered in isolated form. As used herein and unless otherwise indicated, the term "isolated" means that the compounds of Formulas I, Ia, Ib, II, III, and/or IV are separated from other components of either (a) a natural source, such as a plant or cell, such as a bacterial culture, or (b) a synthetic organic chemical reaction mixture, such as by conventional techniques, the compounds of Formulas I, Ia, Ib, II, III, and/or IV are purified.

As used herein and unless otherwise indicated, "purified" means that when isolated, the isolate contains at least 90%, at least 95%, at least 98%, or at least 99% of a compound of Formula I, Ia, Ib, II, III, and/or IV by weight of the isolate.

As used herein and unless otherwise indicated, the term "lyn kinase related disorder" refers to any disorder in a mammal including humans, associated with the altered expression and/or activity of lyn kinase including, but not limited to, cardiovascular disease, dyslipidemia, reducing fat depot levels, dyslipoproteinemia, a disorder of glucose metabolism (i.e., elevated blood glucose levels), metabolic syndrome (i.e., Syndrome X), a PPAR-associated disorder, septicemia, a thrombotic disorder, diabetes, obesity, pancreatitis, hypertension, a renal disease, inflammation, and impotence.

As used herein and unless otherwise indicated, the term "modulate" refers to a change in the expression and/or activity of a protein, such as an enzyme, such as lyn kinase. In an illustrative embodiment, "modulate" refers to increase or decrease the expression and/or activity of a protein, such as an enzyme, such as lyn kinase.

As used herein and unless otherwise indicated, the phrase "pharmaceutically acceptable salt(s)" includes, but is not limited to, salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "phenyl" means —$C_6H_5$. A phenyl group can be unsubstituted or substituted with one or two suitable substituents.

As used herein and unless otherwise indicated, "pre-diabetes" refers to symptoms of diabetes wherein the patient exhibits elevated glucose levels but the full onset of disorders associated with type II diabetes has not yet manifested itself.

As used herein and unless otherwise indicated, a "suitable substituent" means a group that does not nullify the synthetic or pharmaceutical utility of the compounds of Formulas I, Ia, Ib, II, III, and/or IV or the intermediates useful for preparing them. Examples of suitable substituents include, but are not limited to: $(C_1-C_8)$alkyl, $(C_1-C_8)$alkenyl, $(C_1-C_8)$alkynyl, $(C_6)$aryl, $(C_3-C_5)$heteroaryl, $(C_3-C_7)$cycloalkyl, $(C_1-C_8)$ alkoxy, $(C_6)$aryloxy, —CN, —OH, oxo, halo, —$NO_2$, —$CO_2H$, —$NH_2$, —NH(($C_1-C_8$)alkyl), —N(($C_1-C_8$)alkyl)$_2$, —NH(($C_6$)aryl), —N(($C_6$)aryl)$_2$, —CHO, —CO(($C_1-C_8$) alkyl), —CO(($C_6$)aryl), —$CO_2$(($C_1-C_8$)alkyl), and —$CO_2$ (($C_6$)aryl). One of skill in art can readily choose a suitable substituent based on the stability and pharmacological and synthetic activity of a compound of Formula I, Ia, Ib, II, III, and/or IV.

As used herein and unless otherwise indicated, the phrase "therapeutically effective amount" of a composition comprising a compound of Formula I, Ia, Ib, II, III, and/or IV is measured by the therapeutic effectiveness of such a compound, wherein at least one adverse effect of a disorder is ameliorated or alleviated. In one embodiment, the phrase "therapeutically effective amount" of a composition comprising a compound of Formula I, Ia, Ib, II, III, and/or IV is measured by the therapeutic effectiveness of such a compound to alter the expression and/or activity of lyn kinase including, but not limited to up- and down-regulation of this protein. Therapeutically effective amounts of the compounds of Formulas I, Ia, Ib, II, III, and/or IV may up-regulate the expression and/or activity of lyn kinase.

As set forth herein, the invention encompasses methods for treating or preventing a cardiovascular disease, dyslipidemia, dyslipoproteinemia, a disorder of glucose metabolism, Syndrome X, a PPAR-associated disorder, septicemia, a thrombotic disorder, type II diabetes, obesity, pancreatitis, hypertension, a renal disease, inflammation, and impotence, which comprises administering to a mammal in need of such treatment or prevention a therapeutically or prophylactically effective amount of a composition comprising a compound of Formula I, Ia, II, III, and/or IV, or a pharmaceutically acceptable salt thereof, and a pharmaceutically acceptable vehicle.

In some embodiments, the compound is of Formula I

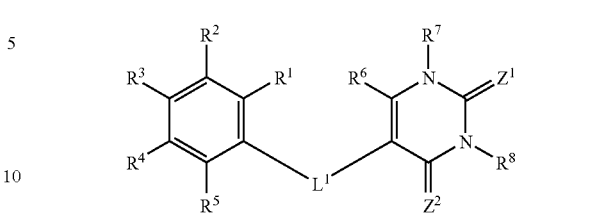

wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{c1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^5$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

or two adjacent groups of R$^1$, R$^2$, R$^3$, R$^4$, and R$^5$ can link to form a fused cycloalkyl or fused heterocycloalkyl group, each optionally substituted by 1, 2, or 3 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^6$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of said C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^7$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$;

R$^8$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$;

R$^{a1}$, R$^{b1}$, R$^{c1}$, and R$^{d1}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

R$^{a2}$, R$^{b2}$, R$^{c2}$, and R$^{d2}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

or R$^{c2}$ and R$^{d2}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy;

Z$^1$ is O, S, or NR$^9$;

R$^9$ is H, OH, C$_{1-6}$alkoxy, C$_{1-6}$haloalkyl, C$_{1-6}$hydroxyalkyl, aryloxy, heteroaryloxy, CN, or NO$_2$;

Z$^2$ is O, S, or NR$^{10}$;

R$^{10}$ is H, OH, C$_{1-6}$alkoxy, C$_{1-6}$haloalkyl, C$_{1-6}$hydroxyalkyl, aryloxy, heteroaryloxy, CN, or NO$_2$;

L$^1$ is O, S, or NR$^{11}$; and

R$^{11}$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$;

or a pharmaceutically acceptable salt thereof.

In some embodiments, the compound is not 5-m-methylphenoxyuracil or a pharmaceutically acceptable salt thereof.

In some embodiments, R$^1$ and R$^5$ are each, independently, H, halo, C$_{1-6}$alkyl, C$_{1-6}$hydroxyalkyl, or C$_{1-6}$haloalkyl. In some embodiments, R$^1$ and R$^5$ are each, independently, H, halo, C$_{1-3}$alkyl, C$_{1-3}$hydroxyalkyl, or C$_{1-3}$haloalkyl. In some embodiments, R$^1$ and R$^5$ are each, independently, H or C$_{1-3}$alkyl. In some embodiments, R$^1$ and R$^5$ are both H.

In some embodiments, R$^2$, R$^3$, and R$^4$ are each, independently, H, halo, C$_{1-6}$alkyl, C$_{1-6}$hydroxyalkyl, or C$_{1-6}$haloalkyl. In some embodiments, R$^2$, R$^3$, and R$^4$ are each, independently, H, C$_{1-6}$alkyl, C$_{1-6}$hydroxyalkyl, or C$_{1-6}$haloalkyl. In some embodiments, R$^2$, R$^3$, and R$^4$ are each, independently, H or C$_{1-6}$alkyl. In some embodiments, R$^2$, R$^3$, and R$^4$ are each, independently, H or C$_{1-3}$alkyl.

In some embodiments, R$^6$ is H, halo, C$_{1-6}$alkyl, C$_{1-6}$hydroxyalkyl, or C$_{1-6}$haloalkyl. In some embodiments, R$^6$ is H or C$_{1-3}$alkyl. In some embodiments, R$^6$ is H.

In some embodiments, R$^7$ is H, C$_{1-6}$alkyl, C(O)R$^{b1}$, C(O)NR$^{c1}$R$^{d1}$, or C(O)OR$^{a1}$. In some embodiments, R$^7$ is H.

In some embodiments, R$^8$ is H, C$_{1-6}$alkyl, C(O)R$^{b1}$, C(O)NR$^{c1}$R$^{d1}$, or C(O)OR$^{a1}$. In some embodiments, R$^8$ is H.

In some embodiments, $Z^1$ is O or S. In some embodiments, $Z^1$ is O. In some embodiments, $Z^1$ is NH, N(OH), N—O—$C_{1-6}$alkyl, N—O-phenyl, CN, or $NO_2$.

In some embodiments, $Z^2$ is O. In some embodiments, $Z^2$ is S. In some embodiments, $Z^2$ is NH, N(OH), N—O—$C_{1-6}$ alkyl, N—O-phenyl, CN, or $NO_2$.

In some embodiments, $L^1$ is O. In some embodiments, $L^1$ is S. In some embodiments, $L^1$ is NH or N($C_{1-6}$alkyl).

In some embodiments, the compound of Formula I has Formula Ia:

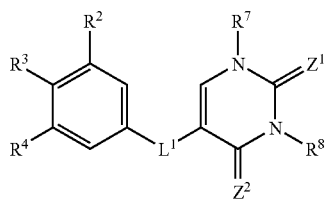

wherein:

$R^2$, $R^3$, and $R^4$ are each, independently, H, halo, $C_{1-6}$alkyl, $C_{1-6}$hydroxyalkyl, or $C_{1-6}$haloalkyl;

$R^7$ is H, $C_{1-6}$alkyl, $C(O)R^{b1}$, $C(O)NR^{c1}R^{d1}$, or $C(O)OR^{a1}$;

$R^8$ is H, $C_{1-6}$alkyl, $C(O)R^{b1}$, $C(O)NR^{c1}R^{d1}$, or $C(O)OR^{a1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O or S;
$Z^2$ is O or S; and
$L^1$ is O or S.

In some embodiments, the compound is not 5-m-methylphenoxyuracil or a pharmaceutically acceptable salt thereof.

In some embodiments, $L^1$ is O. In some embodiments, $L^1$ is S.

In some embodiments, $Z^1$ is O.
In some embodiments, $Z^2$ is O.
In some embodiments, $R^2$, $R^3$ and $R^4$ are each, independently, H, halo, $C_{1-3}$alkyl, $C_{1-3}$hydroxyalkyl, or $C_{1-3}$haloalkyl.

In some embodiments, $R^3$ is H.

In some embodiments, $R^2$ and $R^4$ is halo, $C_{1-3}$alkyl, $C_{1-3}$hydroxyalkyl, or $C_{1-3}$haloalkyl, and the other is H. In some embodiments, $R^2$ and $R^4$ is $C_{1-3}$alkyl, $C_{1-3}$hydroxyalkyl, or $C_{1-3}$haloalkyl, and the other is H. In some embodiments, $R^2$ and $R^4$ is $C_{1-3}$alkyl, and the other is H.

In some embodiments, $R^7$ and $R^8$ are each, independently, H, $C_{1-6}$alkyl, $C(O)$—($C_{1-6}$alkyl), or $C(O)$—O—($C_{1-6}$alkyl).

In some embodiments, $R^7$ and $R^8$ are each, independently, H or $C_{1-3}$alkyl. In some embodiments, $R^7$ and $R^8$ are both H.

In some embodiments, the compound of Formula I has Formula Ib:

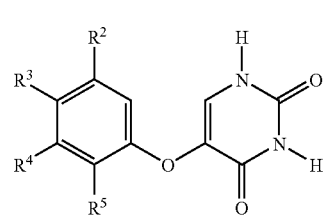

wherein:

$R^2$, $R^3$, $R^4$, and $R^5$ are each, independently, H, F, Cl, $CH_3$, $SCH_3$, $OCH_3$, $C(CH_3)_3$, $CH(CH_3)_2$, or $C_2H_5$.

In some embodiments, $R^2$, $R^3$, $R^4$, and $R^5$ are H.

In some embodiments, $R^2$, $R^4$, and $R^5$ are H, and $R^3$ is $C_2H_5$.

In some embodiments, $R^2$ and $R^5$ are H, $R^3$ is Cl, and $R^4$ is $C_2H_5$.

In some embodiments, $R^2$, $R^4$, and $R^5$ are H, and $R^3$ is $OCH_3$.

In some embodiments, $R^2$ and $R^5$ are H, $R^4$ is $CH_3$, and $R^3$ is $SCH_3$.

In some embodiments, $R^3$, $R^4$, and $R^2$ are H, and $R^5$ is F.

In some embodiments, $R^5$ is H, $R^4$ is $CH_3$, $R^3$ is Cl, and $R^2$ is $CH_3$.

In some embodiments, $R^2$, $R^4$, and $R^5$ are H, and $R^3$ is $C(CH_3)_3$.

In some embodiments, $R^2$, $R^3$, and $R^5$ are H, and $R^4$ is Cl.

In some embodiments, $R^4$ and $R^2$ are H, $R^3$ is $CH_3$, and $R^5$ is $CH_3$.

In some embodiments, $R^2$, $R^4$, and $R^5$ are H, and $R^3$ is $SCH_3$.

In some embodiments, $R^2$, $R^3$, and $R^5$ are H, and $R^4$ is $CH_3$.

In some embodiments, $R^2$ and $R^5$ are H, $R^4$ is $CH_3$, and $R^3$ is Cl.

In some embodiments, $R^2$, $R^4$, and $R^5$ are H, and $R^3$ is $CH(CH_3)_2$.

In some embodiments, the compound is of Formula II, Formula III, or Formula IV:

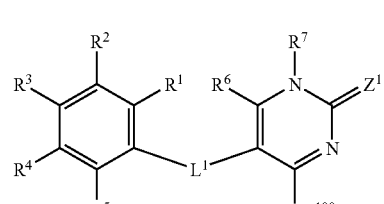

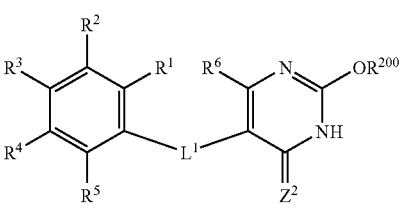

-continued

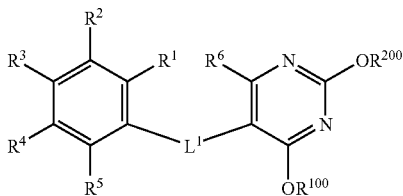
IV wherein:

R¹ is H, halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said C₁₋₆alkyl, C₂₋₆alkenyl, C₂₋₆alkynyl, C₁₋₆haloalkyl, C₁₋₆hydroxyalkyl, C₃₋₆cycloalkyl, aryl, and heteroaryl, is optionally substituted by 1, 2, 3, 4, or 5 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R² is H, halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said C₁₋₆alkyl, C₂₋₆alkenyl, C₂₋₆alkynyl, C₁₋₆haloalkyl, C₁₋₆hydroxyalkyl, C₃₋₆cycloalkyl, aryl, and heteroaryl, is optionally substituted by 1, 2, 3, 4, or 5 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R³ is H, halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said C₁₋₆alkyl, C₂₋₆alkenyl, C₂₋₆alkynyl, C₁₋₆haloalkyl, C₁₋₆hydroxyalkyl, C₃₋₆cycloalkyl, aryl, and heteroaryl, is optionally substituted by 1, 2, 3, 4, or 5 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁴ is H, halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said C₁₋₆alkyl, C₂₋₆alkenyl, C₂₋₆alkynyl, C₁₋₆haloalkyl, C₁₋₆hydroxyalkyl, C₃₋₆cycloalkyl, aryl, and heteroaryl, is optionally substituted by 1, 2, 3, 4, or 5 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁵ is H, halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said C₁₋₆alkyl, C₂₋₆alkenyl, C₂₋₆alkynyl, C₁₋₆haloalkyl, C₁₋₆hydroxyalkyl, C₃₋₆cycloalkyl, aryl, and heteroaryl, is optionally substituted by 1, 2, 3, 4, or 5 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

or two adjacent groups of R¹, R², R³, R⁴, and R⁵ can link to form a fused cycloalkyl or fused heterocycloalkyl group, each optionally substituted by 1, 2, or 3 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁶ is H, halo, C₁₋₆alkyl, C₂₋₆alkenyl, C₂₋₆alkynyl, C₁₋₆haloalkyl, C₁₋₆hydroxyalkyl, C₃₋₆cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said C₁₋₆alkyl, C₂₋₆alkenyl, C₂₋₆alkynyl, C₁₋₆haloalkyl, C₁₋₆hydroxyalkyl, C₃₋₆cycloalkyl, aryl, and heteroaryl, is optionally substituted by 1, 2, 3, 4, or 5 substituents independently selected from halo, C₁₋₆alkyl, C₂₋₆alkenyl, C₂₋₆alkynyl, C₁₋₆haloalkyl, C₁₋₆hydroxyalkyl, C₃₋₆cycloalkyl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁷ is H, C₁₋₆alkyl, C₁₋₆haloalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)₂R$^{b1}$, or S(O)₂NR$^{c1}$R$^{d1}$;

R$^{a1}$, R$^{b1}$, R$^{c1}$, and R$^{d1}$ are each, independently, selected from H, C₁₋₆alkyl, C₁₋₆haloalkyl, C₁₋₆hydroxyalkyl, C₂₋₆alkenyl, C₂₋₆alkynyl, aryl, cycloalkyl, heteroaryl, heterocycloalkyl, arylalkyl, heteroarylalkyl, cycloalkylalkyl, and heterocycloalkylalkyl, wherein each of said C₁₋₆alkyl, C₁₋₆haloalkyl, C₁₋₆hydroxyalkyl, C₂₋₆alkenyl, C₂₋₆alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{100}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

each $R^{f1}$ is, independently, H, $C_{1-6}$alkyl, $C_{1-6}$haloalkyl, $C_{1-6}$hydroxyalkyl, $C_{2-6}$alkenyl, $(C_{1-6}$alkoxy)-$C_{1-6}$alkyl, $C_{2-6}$alkynyl, aryl, cycloalkyl, heteroaryl, heterocycloalkyl, arylalkyl, cycloalkylalkyl, heteroarylalkyl, or heterocycloalkylalkyl;

each $R^{g1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, or heterocycloalkyl; and each $R^{h1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

or a pharmaceutically acceptable salt thereof.

In some embodiments, for a compound of Formula II, when $Z^1$ is O or S, $R^7$ is H, and $L^1$ is O, S, or $NR^{11}$, wherein $R^{11}$ is H or $C_{1-6}$alkyl, then $R^{100}$ is not $C_{1-6}$alkyl or aryl.

In some embodiments, $R^1$ and $R^5$ are each, independently, H, halo, $C_{1-6}$alkyl, $C_{1-6}$hydroxyalkyl, or $C_{1-6}$haloalkyl. In some embodiments, $R^1$ and $R^5$ are each, independently, H, halo, $C_{1-3}$alkyl, $C_{1-3}$hydroxyalkyl, or $C_{1-3}$haloalkyl. In some embodiments, $R^1$ and $R^5$ are each, independently, H or $C_{1-3}$alkyl. In some embodiments, $R^1$ and $R^5$ are both H.

In some embodiments, $R^2$, $R^3$, and $R^4$ are each, independently, H, halo, $C_{1-6}$alkyl, $C_{1-6}$hydroxyalkyl, or $C_{1-6}$haloalkyl. In some embodiments, $R^2$, $R^3$, and $R^4$ are each, independently, H, $C_{1-6}$alkyl, $C_{1-6}$hydroxyalkyl, or $C_{1-6}$haloalkyl. In some embodiments, $R^2$, $R^3$, and $R^4$ are each, independently, H or $C_{1-6}$alkyl. In some embodiments, $R^2$, $R^3$, and $R^4$ are each, independently, H or $C_{1-3}$alkyl.

In some embodiments, $R^6$ is H, halo, $C_{1-6}$alkyl, $C_{1-6}$hydroxyalkyl, or $C_{1-6}$haloalkyl. In some embodiments, $R^6$ is H or $C_{1-3}$alkyl. In some embodiments, $R^6$ is H.

In some embodiments, $R^7$ is H, $C_{1-6}$alkyl, $C(O)R^{b1}$, $C(O)NR^{c1}R^{d1}$, or $C(O)OR^{a1}$. In some embodiments, $R^7$ is H.

In some embodiments, $Z^1$ is O or S. In some embodiments, $Z^1$ is O. In some embodiments, $Z^1$ is NH, N(OH), N—O—$C_{1-6}$alkyl, N—O-phenyl, CN, or $NO_2$.

In some embodiments, $Z^2$ is O. In some embodiments, $Z^2$ is S. In some embodiments, $Z^2$ is NH, N(OH), N—O—$C_{1-6}$alkyl, N—O-phenyl, CN, or $NO_2$.

In some embodiments, $L^1$ is O. In some embodiments, $L^1$ is S. In some embodiments, $L^1$ is NH or N($C_{1-6}$alkyl).

In some embodiments, $R^{100}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, or heteroaryl, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, $R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, or heteroaryl, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

An illustrative example of a compound that is encompassed by Formulas I and Ia includes, but is not limited to:

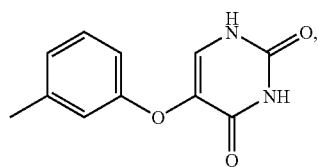

101 which is also known as 5-(m-tolyloxy)pyrimidine-2,4(1H, 3H)-dione.

It will be understood that above compounds are illustrative only and not intended to limit the scope of the claims to only those compounds.

The compounds of Formulas I, Ia, Ib, II, III, and/or IV can be synthesized by organic chemistry techniques known to those of ordinary skill in the art, for example as described in U.S. Pat. Nos. 3,922,345 and 4,080,454, each of which is incorporated herein by reference in its entirety.

Preparation of compounds of Formulas I, Ia, Ib, II, III, and/or IV can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3$^{rd}$ Ed., Wiley & Sons, Inc., New York (1999), which is incorporated herein by reference in its entirety. Suitable hydroxyl protecting groups include, but are not limited to, tert-butyldimethylsilyl (TBS), methoxymethyl ether (MOM), tetrahydropyranyl ether (THP), t-Butyl ether, allyl ether, benzyl ether, t-Butyldimethylsilyl ether (TBDMS), t-Butyldiphenylsilyl ether (TBDPS), acetic acid ester, and the like.

The invention provides compounds that may be effective in modulating the expression and/or activity of lyn kinase both in vitro and in vivo. The compounds of Formulas I, Ia, Ib, II, III, and/or IV may be effective in modulating lyn kinase. Without being limited by theory, it is believed that modulation of lyn kinase expression and/or activity is useful in treating or preventing a disorder associated with abnormal blood glucose levels, weight gain, or fat depot levels. The invention further provides compositions and formulations comprising one or more compounds that may be useful in modulating lyn kinase activity. The invention also encompasses methods of modulating lyn kinase activity comprising administering to a subject, such as a mammal, including a human, in need of treatment or prevention, a therapeutically or prophylactically effective amount of a compound of Formula I, Ia, Ib, II, III, and/or IV to modulate the activity of lyn kinase.

In one embodiment, a compound of Formula I, Ia, Ib, II, III, and/or IV, or a composition comprising the same and a pharmaceutically acceptable vehicle, is administered to a mammal, such as a human, with a cardiovascular disease, a dyslipidemia, a dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, or impotence.

In one embodiment, "treatment" or "treating" refers to an amelioration of a disease or disorder, or at least one discernible symptom thereof, preferably associated with lyn kinase. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In some embodiments, the compositions comprising a compound of Formula I, Ia, Ib, II, III, and/or IV are administered to a patient, such as a human, as a preventative measure against such diseases. As used herein and unless otherwise indicated, "prevention" or "preventing" refers to a reduction of the risk of acquiring a given disease or disorder. In one mode of the embodiment, the compositions of the present invention are administered as a preventative measure to a patient, preferably a human having a genetic predisposition to a cardiovascular disease, a dyslipidemia, a dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, or impotence. Examples of such genetic predispositions include, but are not limited to, the ε4 allele of apolipoprotein E; a loss of function or null mutation in the lipoprotein lipase gene coding region or promoter (e.g., mutations in the coding regions resulting in the substitutions D9N and N291 S; for a review of genetic mutations in the lipoprotein lipase gene that increase the risk of cardiovascular diseases, dyslipidemias and dyslipoproteinemias, see, e.g., Hayden et al., Mol. Cell Biochem., 1992, 113, 171-176); and familial combined hyperlipidemia and familial hypercholesterolemia.

In another illustrative embodiment, the compositions comprising a compound of Formula I, Ia, Ib, II, III, and/or IV are administered as a preventative measure to a subject having a non-genetic predisposition to a cardiovascular disease, a dyslipidemia, a dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, or impotence. Examples of such non-genetic predispositions include, but are not limited to, cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions comprising a compound of Formulas I, Ia, Ib, II, III, and/or IV may be used for the prevention of one disease or disorder and concurrently treating another (e.g., prevention of polycystic ovarian disease while treating diabetes; prevention of impotence while treating a cardiovascular disease). In one particular embodiment, the methods of the invention do not encompass treating or preventing asthma.

The present invention provides methods for the treatment or prevention of a cardiovascular disease, comprising administering to a patient a therapeutically effective amount of a composition comprising a compound of Formula I, Ia, Ib, II, III, and/or IV and a pharmaceutically acceptable vehicle. In some embodiments, the cardiovascular disease is associated with abnormal/altered lyn kinase activity and/or expression. As used herein and unless otherwise indicated, the term "cardiovascular diseases" refers to diseases of the heart and circulatory system. These diseases are often associated with dyslipoproteinemias and/or dyslipidemias. Cardiovascular diseases, which the compositions comprising a compound of Formula I, Ia, Ib, II, III, and/or IV are useful for preventing or treating include, but are not limited to, arteriosclerosis; atherosclerosis; stroke; ischemia; endothelium dysfunctions, in particular those dysfunctions affecting blood vessel elasticity; peripheral vascular disease; coronary heart disease; myocardial infarction; cerebral infarction and restenosis.

The present invention provides methods for the treatment or prevention of a dyslipidemia comprising administering to a patient a therapeutically effective amount of a composition comprising a compound of Formula I, Ia, Ib, II, III, and/or IV and a pharmaceutically acceptable vehicle. In some embodiments, the dyslipidemia is associated with abnormal/altered lyn kinase activity and/or expression. As used herein and unless otherwise indicated, the term "dyslipidemias" refers to disorders that lead to or are manifested by aberrant levels of circulating lipids. To the extent that levels of lipids in the blood are too high, the compositions comprising a compound of Formula I, Ia, Ib, II, III, and/or IV are administered to a patient to restore normal levels. Normal levels of lipids are reported in medical treatises known to those of skill in the art. For example, recommended blood levels of LDL, HDL, free triglycerides and others parameters which are used to diagnose dyslipidemia can be found at the web site of the American Heart Association and that of the National Cholesterol Education Program of the National Heart, Lung and Blood Institute. At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include, but are not limited to, hyperlipidemia and low blood levels of high density lipoprotein (HDL) cholesterol. In some embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g., β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, for example, reducing LDL in the blood of a patient, reducing free triglycerides in the blood of a patient, increasing the ratio of HDL to LDL in the blood of a patient, and inhibiting saponified and/or non-saponified fatty acid synthesis, comprising administering to the patient a composition comprising a compound of Formula I, Ia, Ib, II, III, and/or IV in an amount effective alter lipid metabolism.

The present invention provides methods for the treatment or prevention of a dyslipoproteinemia comprising administering to a patient a therapeutically effective amount of a composition comprising a compound of Formula I, Ia, Ib, II, III, and/or IV and a pharmaceutically acceptable vehicle. As used herein and unless otherwise indicated, the term "dyslipoproteinemias" refers to disorders that lead to or are manifested by aberrant levels of circulating lipoproteins. To the extent that levels of lipoproteins in the blood are too high, the compositions comprising a compound of Formula I, Ia, Ib, II, III, and/or IV are administered to a patient to restore normal levels. Conversely, to the extent that levels of lipoproteins in the blood are too low, the compositions comprising a compound of Formula I, Ia, Ib, II, III, and/or IV are administered to a patient to restore normal levels. Normal levels of lipoproteins are reported in medical treatises known to those of skill in the art.

Dyslipoproteinemias, which the compositions of the present invention are useful for preventing or treating include, but are not limited to, high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with type II diabetes, obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a composition comprising a compound of Formula I, Ia, Ib, II, III, and/or IV in an amount effective to bring about reduction, elevation or promotion, respectively.

The present invention provides methods for the treatment or prevention of a glucose metabolism disorder, comprising administering to a patient a therapeutically effective amount of a compound, or composition comprising a compound of Formula I, Ia, Ib, II, III, and/or IV and a pharmaceutically acceptable vehicle. As used herein and unless otherwise indicated, the term "glucose metabolism disorders" refers to disorders that lead to or are manifested by aberrant glucose storage and/or utilization. To the extent that indicia of glucose metabolism (i.e., blood insulin, blood glucose) are too high, the compositions comprising a compound of Formula I, Ia, Ib, II, III, and/or IV are administered to a patient to restore normal levels. Conversely, to the extent that indicia of glucose metabolism are too low, the compositions comprising a compound of Formula I, Ia, Ib, II, III, and/or IV are administered to a patient to restore normal levels. Normal indicia of glucose metabolism are reported in medical treatises known to those of skill in the art. In some embodiments, the glucose metabolism disorder is associated with abnormal/altered lyn kinase activity and/or expression.

Glucose metabolism disorders which the compositions of the present invention are useful for preventing or treating include, but are not limited to, impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; and high levels of blood insulin and/or glucose.

The present invention further provides methods for altering glucose metabolism in a patient, for example to increase insulin sensitivity and/or oxygen consumption of a patient, comprising administering to the patient a compound, or composition comprising a compound of Formula I, Ia, Ib, II, III, and/or IV, in an amount effective to alter glucose metabolism.

The present invention provides methods for the treatment or prevention of a peroxisome proliferative activated receptor ("PPAR")-associated disorder, comprising administering to a patient a therapeutically effective amount of a compound, or composition comprising a compound of Formula I, Ia, Ib, II, III, and/or IV and a pharmaceutically acceptable vehicle. In some embodiments, the PPAR-associated disorder is associated with abnormal/altered lyn kinase activity and/or expression. As used herein and unless otherwise indicated, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-J; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

The present invention provides methods for the treatment or prevention of a renal disease, comprising administering to a patient a therapeutically effective amount of a compound, or composition comprising a compound of Formula I, Ia, Ib, II, III, and/or IV and a pharmaceutically acceptable vehicle. In some embodiments, the renal disease is associated with abnormal/altered lyn kinase activity and/or expression. Renal diseases that can be treated by the compounds of the present invention include glomerular diseases (including, but not limited to, acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including, but not limited to, acute tubular necrosis and acute renal failure, polycystic renal diseasemedullary sponge kidney, medullary cystic disease, nephrogenic diabetes, and renal tubular acidosis), tubulointerstitial diseases (including, but not limited to, pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including, but not limited to, renal cell carcinoma and nephroblastoma). In one embodiment, renal diseases that are treated by the compounds of the present invention are vascular diseases including, but not limited to, hypertension, nephrosclerosis, microangiopathic hemolytic anemia, atheroembolic renal disease, diffuse cortical necrosis, and renal infarcts.

As used herein and unless otherwise indicated, "treatment or prevention of Syndrome X or Metabolic Syndrome" encompasses treatment or prevention of a symptom associated with metabolic syndrome including, but not limited to, impaired glucose tolerance, hypertension and dyslipidemia and/or dyslipoproteinemia. In some embodiments, the metabolic syndrome is associated with abnormal/altered lyn kinase activity and/or expression.

Metabolic syndrome is characterized by a group of metabolic risk factors in a person. Risk factors that are associated with metabolic syndrome that can be treated or prevented by administering a compound, or composition comprising a compound of Formula I, Ia, Ib, II, III, and/or IV include, but are not limited to, central obesity (i.e., excessive fat tissue in and around the abdomen); atherogenic dyslipidemia (blood fat disorders—mainly high triglycerides and low HDL cholesterol—that foster plaque buildups in artery walls); raised blood pressure (130/85 mmHg or higher); insulin resistance or glucose intolerance (the body cannot properly use insulin or blood sugar); prothrombotic state (e.g., high fibrinogen or plasminogen activator inhibitor in the blood); and a proinflammatory state (e.g., elevated high-sensitivity C-reactive protein in the blood).

The underlying causes of this syndrome are overweight/obesity, physical inactivity and genetic factors. People with metabolic syndrome are at increased risk of coronary heart disease, other diseases related to plaque buildups in artery walls (e.g., stroke and peripheral vascular disease) and type 2 diabetes.

Metabolic syndrome is closely associated with a generalized metabolic disorder called insulin resistance, in which the body cannot use insulin efficiently. This may be why the metabolic syndrome is also called the insulin resistance syndrome.

Some people are genetically predisposed to insulin resistance. Acquired factors, such as excess body fat and physical inactivity, can elicit insulin resistance and the metabolic syndrome in these people. Many people with insulin resistance have central obesity. The biologic mechanisms at the molecular level between insulin resistance and metabolic risk factors are not fully understood and appear to be complex.

The compositions comprising a compound of Formula I, Ia, Ib, II, III, and/or IV may therefore be useful in treating or preventing metabolic syndrome and disorders and risk factors associated with metabolic syndrome.

As used herein and unless otherwise indicated, "treatment or prevention of diabetes" encompasses treatment or prevention of a complication associated with type II diabetes including, but not limited to, retinopathy (i.e., blindness); neuropathy (i.e., nerve damage) which leads to foot ulcers, gangrene, and amputations; kidney damage, which leads to dialysis; and cardiovascular disease. In some embodiments, the type II diabetes is associated with abnormal/altered lyn kinase activity and/or expression.

Type II diabetes is associated with obesity and with aging. It is a lifestyle-dependent disease, and has a strong genetic component (concordance in twins is 80-90%). The problem seems not so much in insulin production, but that when the insulin reaches its target cells, it does not work correctly. Most Type II diabetes patients initially have high insulin levels along with high blood sugar. However, since sugar signals the pancreas to release insulin, Type II diabetics eventually become resistant to that signal and the endocrine-pancreas soon will not make enough insulin. These people end up managing the disease with insulin and they need much higher doses because they are resistant to it.

When a person takes in a high load of sugar, the sugar stimulates the pancreas to release insulin. The targets for insulin are muscle, fat, and liver cells. These cells have insulin receptor sites on the outside of the cell membrane. For most people, when insulin has bound to the receptors, a cascade of events begins, which leads to sugar being transported from the blood into the interior of the cell. In Type II diabetics, even when insulin is present on the cell membrane, the process doesn't work. The glucose is never taken up into the cell and remains in the bloodstream.

The liver is responsible for glucose production and insulin is the regulatory agent of production. A high blood sugar content causes the pancreas to release insulin, and the insulin should signal the liver to stop making sugars. But, in diabetics, there's resistance to that signal and the liver keeps producing glucose. Hyperglycemia leads to glucose toxicity.

It is not high blood sugar that is the disease process of diabetes, but complications from the high blood sugar. A major problem faced by doctors is that some people with high blood sugar feel fine; it is hard to treat diseases that are asymptomatic since most people do not want to take a pill for something that they do not feel bad about. The compositions comprising a compound of Formula I, Ia, Ib, II, III, and/or IV may therefore be useful in treating or preventing type II diabetes or complications arising from type II diabetes and disorders and risk factors associated with metabolic syndrome. Complications of diabetes include, but are not limited to, diabetic neuropathy, diabetic retinopathy, erectile dysfunction, and kidney disease and the compounds of Formulas I, Ia, Ib, II, III, and/or IV are useful in treating or preventing these complications.

As used herein and unless otherwise indicated, "treatment or prevention of obesity" encompasses treatment or prevention of a complication associated with obesity. Complications of obesity include, but are not limited to, hypercholesterolemia, hypertension, dyslipidemia (for example, high total cholesterol or high levels of triglycerides), type 2 diabetes, coronary heart disease, stroke, gallbladder disease, osteoarthritis, sleep apnea and respiratory problems, and some cancers (endometrial, breast, and colon). In some embodiments, the obesity is associated with abnormal/altered lyn kinase activity and/or expression The present invention provides methods for the treatment or prevention of septicemia, thrombotic disorders, pancreatitis, hypertension, inflammation, and impotence, comprising administering to a patient a therapeutically effective amount of a compound, or composition comprising a compound of Formula I, Ia, Ib, II, III, and/or IV and a pharmaceutically acceptable vehicle. In some embodiments, these disorders are associated with abnormal/altered lyn kinase activity and/or expression.

As used herein and unless otherwise indicated, "treatment or prevention of septicemia" encompasses treatment or prevention of septic shock.

As used herein and unless otherwise indicated, "treatment or prevention of thrombotic disorders" encompasses treatment or prevention of high blood levels of fibrinogen and promotion of fibrinolysis.

In addition to treating or preventing obesity, the compositions comprising a compound of Formula I, Ia, Ib, II, III, and/or IV can be administered to an individual to promote weight reduction of the individual.

In some embodiments, the subject has abnormal/altered lyn kinase activity and/or expression but does not exhibit or manifest any physiological symptoms associated with a lyn-kinase-related disease.

The invention provides methods of treatment and prophylaxis by administration to a patient of a therapeutically effective amount of a composition comprising a compound of Formula I, Ia, Ib, II, III, and/or IV. The patient may be a mammal, including, but not limited to, an animal such a cow, horse, sheep, pig, chicken, turkey, quail, cat, dog, mouse, rat, rabbit, guinea pig, etc. In some embodiments, the patient or subject is a human.

The present compositions, which comprise one or more compounds of Formulas I, Ia, Ib, II, III, and/or IV, can be administered orally. The compounds of Formulas I, Ia, Ib, II, III, and/or IV may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of Formula I, Ia, Ib, II, III, and/or IV. In certain embodiments, more than one compound of Formula I, Ia, Ib, II, III, and/or IV is administered to a patient. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The desired mode of administration is left to the discretion of the practitioner, and will depend in-part upon the site of the medical condition. In most instances, administration may result in the release of the compounds of Formulas I, Ia, Ib, II, III, and/or IV into the bloodstream.

In specific embodiments, it may be desirable to administer one or more compounds of Formulas I, Ia, Ib, II, III, and/or IV locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of Formulas I, Ia, Ib, II, III, and/or IV can be formulated as a suppository, with traditional binders and vehicles such as triglycerides.

In another embodiment, the compounds of Formulas I, Ia, Ib, II, III, and/or IV can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of Formulas I, Ia, Ib, II, III, and/or IV can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds of Formulas I, Ia, Ib, II, III, and/or IV, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

The present compositions will contain a therapeutically effective amount of a compound of Formula I, Ia, Ib, II, III, and/or IV, optionally more than one compound of Formula I, Ia, Ib, II, III, and/or IV, such as in purified form, together with a suitable amount of a pharmaceutically acceptable vehicle so as to provide the form for proper administration to the patient.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of Formula I, Ia, Ib, II, III, and/or IV is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of Formulas I, Ia, Ib, II, III, and/or IV and pharmaceutically acceptable vehicles are preferably sterile. Water is a suitable vehicle when the compound of Formula I, Ia, Ib, II, III, and/or IV is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, A.R. Gennaro (Editor) Mack Publishing Co.

In one embodiment, the compounds of Formulas I, Ia, Ib, II, III, and/or IV are formulated in accordance with routine procedures as a pharmaceutical composition adapted for intravenous administration to human beings. Typically, compounds of Formulas I, Ia, Ib, II, III, and/or IV for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of Formula I, Ia, Ib, II, III, and/or IV is to be administered by infusion, it can be dispensed, for example, with an infusion bottle containing sterile pharmaceutical grade water or saline. Where the compound of Formula I, Ia, Ib, II, III, and/or IV is administered by injection, an ampoule of sterile water for injection or saline can be provided so that the ingredients may be mixed prior to administration.

The compounds and compositions of the invention be administered orally. Compounds and compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of Formulas I, Ia, Ib, II, III, and/or IV. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are suitably of pharmaceutical grade.

The amount of a compound of Formula I, Ia, Ib, II, III, and/or IV that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of Formula I, Ia, Ib, II, III, and/or IV per kilogram body weight. In some embodiments of the invention, the oral dose is 0.01 milligram to 70 milligrams per kilogram body weight, or 0.1 milligram to 50 milligrams per kilogram body weight, or 0.5 milligram to 20 milligrams per kilogram body weight, or 1 milligram to 10 milligrams per kilogram body weight. In some embodiments, the oral dose is 5 milligrams of a compound of Formula I, Ia, Ib, II, III, and/or IV per kilogram body weight. The dosage amounts described herein refer to total amounts administered; that is, if more than one compound of Formula I, Ia, Ib, II, III, and/or IV is administered, the dosages correspond to the total amount of the compounds of Formulas I, Ia, Ib, II, III, and/or IV administered. Oral compositions can contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of Formula I, Ia, Ib, II, III, and/or IV per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of Formulas I, Ia, Ib, II, III, and/or IV for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of Formulas I, Ia, Ib, II, III, and/or IV. Optionally associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kit contains more than one compound of Formula I, Ia, Ib, II, III, and/or IV. In some embodiments, the kit comprises a compound of Formula I, Ia, Ib, II, III, and/or IV and another lipid-mediating compound, including but not limited to a statin, a thiazolidinedione, or a fibrate.

The compounds of Formulas I, Ia, Ib, II, III, and/or IV can be assayed in vitro and in vivo, for the desired therapeutic or prophylactic activity, prior to use in humans. For example, in vitro assays can be used to determine whether administration of a specific compound of Formula I, Ia, Ib, II, III, and/or IV or a combination of compounds of Formulas I, Ia, Ib, II, III, and/or IV is suitable for lowering fatty acid synthesis. The compounds of Formulas I, Ia, Ib, II, III, and/or IV may also be demonstrated to be effective and safe using animal model systems. Other methods will be known to the skilled artisan and are within the scope of the invention.

In some embodiments of the invention, the compounds of Formulas I, Ia, Ib, II, III, and/or IV can be used in combination therapy with at least one other therapeutic agent. The compound of Formula I, Ia, Ib, II, III, and/or IV and the therapeutic agent can act additively or synergistically. In one embodiment, a composition comprising a compound of Formula I, Ia, Ib, II, III, and/or IV is administered concurrently with the administration of another therapeutic agent, which can be part of the same composition as the compound of Formula I, Ia, Ib, II, III, and/or IV or a different composition. In another embodiment, a composition comprising a compound of Formula I, Ia, Ib, II, III, and/or IV is administered prior or subsequent to administration of another therapeutic agent. As many of the disorders for which the compounds of Formulas I, Ia, Ib, II, III, and/or IV are useful in treating are chronic disorders, in one embodiment combination therapy involves alternating between administering a composition comprising a compound of Formula I, Ia, Ib, II, III, and/or IV and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds of Formulas I, Ia, Ib, II, III, and/or IV include, but are not limited to, atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds of Formulas I, Ia, Ib, II, III, and/or IV include but are not limited to 5-((4-(2-(methyl-2-pyridinylamino)ethoxy)phenyl)methyl)-2,4-thiazolidinedione, troglitazone, pioglitazone, ciglitazone, WAY-120,744, englitazone, AD 5075, darglitazone, and rosiglitazone. Fibrates for use in combination with the compounds of Formulas I, Ia, Ib, II, III, and/or IV include but are not limited to gemfibrozil, fenofibrate, clofibrate, or ciprofibrate. As mentioned previously, a therapeutically effective amount of a fibrate or thiazolidinedione often has toxic side effects. Accordingly, in some embodiments of the present invention, when a composition of the invention is administered in combination with a PPAR agonist, the dosage of the PPAR agonist is below that which is accompanied by toxic side effects.

The present compositions can also be administered together with a bile-acid-binding resin. Bile-acid-binding resins for use in combination with the compounds of Formulas I, Ia, Ib, II, III, and/or IV include, but are not limited to, cholestyramine and colestipol hydrochloride.

The present compositions can also be administered together with niacin or nicotinic acid.

The present compositions can also be administered together with a RXR agonist. RXR agonists for use in combination with the compounds of Formulas I, Ia, Ib, II, III, and/or IV include, but are not limited to, LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, or 4-((3,5,5,8,8-pentamethyl-5,6,7,8-tetrahydro-2-naphthyl)2-carbonyl)-benzoic acid.

The present compositions can also be administered together with an anti-obesity drug. Anti-obesity drugs for use in combination with the compounds of Formulas I, Ia, Ib, II, III, and/or IV include, but are not limited to, β-adrenergic receptor agonists, such as β-3 receptor agonists, sibutramine, bupropion, fluoxetine, and phentermine.

The present compositions can also be administered together with a hormone. Hormones for use in combination with the compounds of Formulas I, Ia, Ib, II, III, and/or IV include, but are not limited to, thyroid hormone, estrogen and insulin. Suitable insulins include, but are not limited to, injectable insulin, transdermal insulin, inhaled insulin, or any combination thereof. As an alternative to insulin, an insulin derivative, secretagogue, sensitizer or mimetic may be used. Insulin secretagogues for use in combination with the compounds of Formulas I, Ia, Ib, II, III, and/or IV include but are not limited to forskolin, dibutryl cAMP or isobutylmethylxanthine (IBMX).

The present compositions can also be administered together with a tyrophostine or an analog thereof. Tyrophostines for use in combination with the compounds of Formulas I, Ia, Ib, II, III, and/or IV include, but are not limited to, tryophostine 51.

The present compositions can also be administered together with sulfonylurea-based drugs. Sulfonylurea-based drugs for use in combination with the compounds of Formulas I, Ia, Ib, II, III, and/or IV include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

The present compositions can also be administered together with a biguanide. Biguanides for use in combination with the compounds of Formulas I, Ia, Ib, II, III, and/or IV include, but are not limited to, metformin, phenformin and buformin.

The present compositions can also be administered together with an α-glucosidase inhibitor. α-glucosidase inhibitors for use in combination with the compounds of Formulas I, Ia, Ib, II, III, and/or IV include, but are not limited to, acarbose and miglitol.

The present compositions can also be administered together with an apo A-I agonist. In one embodiment, the apo A-J agonist is the Milano form of apo A-I (apo A-IM). In one embodiment, the apo A-IM for administration in conjunction with the compounds of Formulas I, Ia, Ib, II, III, and/or IV is produced by the method of U.S. Pat. No. 5,721,114 to Abrahamsen. In another embodiment, the apo A-I agonist is a peptide agonist. In another embodiment, the apo A-I peptide agonist for administration in conjunction with the compounds of Formulas I, Ia, Ib, II, III, and/or IV is a peptide of U.S. Pat. No. 6,004,925 or 6,037,323 to Dasseux.

The present compositions can also be administered together with apolipoprotein E (apo E). In one embodiment, the apoE for administration in conjunction with the compounds of Formulas I, Ia, Ib, II, III, and/or IV is produced by the method of U.S. Pat. No. 5,834,596.

In yet other embodiments, the present compositions can be administered together with an HDL-raising drug; an HDL enhancer; or a regulator of the apolipoprotein A-I, apolipoprotein A-IV and/or apolipoprotein genes.

The present compositions can be administered together with a known cardiovascular drug. Cardiovascular drugs for use in combination with the compounds of Formulas I, Ia, Ib, II, III, and/or IV to prevent or treat cardiovascular diseases include, but are not limited to, peripheral anti-adrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

The present compositions can be administered together with treatment with irradiation or one or more chemotherapeutic agents. For irradiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., $2^{nd}$. Ed., J.B. Lippencott Company, Philadelphia. Useful chemotherapeutic agents include, but are not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In one embodiment, a composition of the invention further comprises one or more chemotherapeutic agents and/or is administered concurrently with radiation therapy. In another embodiment, chemotherapy or radiation therapy is administered prior or subsequent to administration of a present composition, such as at least an hour, five hours, 12 hours, a day, a week, a month, or several months (e.g., up to three months), subsequent to administration of a composition of the invention.

EXAMPLES

Type II diabetes is characterized by high blood glucose levels in the presence of normal amounts of insulin. Animal models of type II diabetes involve administering high levels of glucose and measuring blood glucose levels and the ability of the experimental animal to maintain glucose homeostasis over time. Several pharmacological structural classes can effectively regulate this hyperglycemic response including sulfonylureas, thiazoladinediones (PPARγ agonists; glitazones) or metformin (glucophage). These drug classes are also clinically approved for use in humans. In one present study, a mouse model of hyperglycemia has been established by administering high levels of glucose to mice. This model was validated as a model of type II diabetes by demonstrating that metformin can effectively reduce the blood glucose load. Compound 101, which is an illustrative example of a compound of Formula I, Ia, Ib, II, III, and/or IV, is effective in reducing blood glucose levels in this model of type II diabetes.

Example 1

Oral Glucose Tolerance Test (Actual Example)

CD1 male mice (Harlan, Indianapolis, Ind.) of between 8 and 10 weeks of age were fasted 18 hours prior to the start of the study. All blood glucose levels were measured using an Accu-Check Aviva glucose monitors with Aviva glucose test strips from a blood drop derived from the mouse tail. Prior to any treatment, baseline levels of blood glucose were measured in fasted mice. Thirty minutes after baseline measurement, Compound 101 or vehicle was administered via intravenous administration. Thirty minutes after compound administration, animals were administered an oral solution (via gavage) of glucose in distilled water. The dose of glucose was 1.5 g/Kg of body weight. Blood glucose levels were measured 15, 30, 60, 90 and 120 minutes after glucose challenge. There were 6 mice per treatment group. Representation of the experimental and control groups are summarized in Table I:

TABLE I

| TREATMENT | N = NUMBER OF MICE |
|---|---|
| Vehicle Control | 6 |
| 5-M-toloxyuracil (7 mg/kg) | 6 |

Representation of the treatment and time points for administration for the experimental protocol are summarized in Table II:

TABLE II

| TREATMENT | TIME |
|---|---|
| Measure Baseline Blood Glucose Level | 0 minutes |
| Drug or Vehicle Treatment | 30 minutes |
| Administer Oral Glucose Solution | 60 minutes |
| Measure Blood Glucose | 75 minutes |
| Measure Blood Glucose | 90 minutes |
| Measure Blood Glucose | 120 minutes |
| Measure Blood Glucose | 150 minutes |
| Measure Blood Glucose | 180 minutes |

Blood glucose levels were taken from treated and untreated groups at the times above and measured for concentration of glucose in milligram per deciliter of blood of sample. Average values were calculated for each time point from each group and summarized after performing statistical analysis in Table III below:

TABLE III

| TREATMENT | TIME | VEHICLE BLOOD GLUCOSE LEVELS (MG/DL) AVG ± SEM | COMPOUND 101 BLOOD GLUCOSE LEVELS (MG/DL) AVG ± SEM |
|---|---|---|---|
| Measure Baseline Blood Glucose Level | 0 min | 58.5 ± 18.0 | 62.0 ± 13.1 |
| Drug or Vehicle Treatment | 30 minutes | N/A | N/A |
| Administer Oral Glucose Solution | 60 minutes | N/A | N/A |
| Measure Blood Glucose | 75 minutes | 179 ± 54.8 | 119.6 ± 36.0 |
| Measure Blood Glucose | 90 minutes | 212.5 ± 52.8 | 156.4 ± 55.9 |
| Measure Blood Glucose | 120 minutes | 199.5 ± 45.1 | 152.2 ± 33.9 |
| Measure Blood Glucose | 150 minutes | 173.5 ± 41.3 | 107.8 ± 34.1 |
| Measure Blood Glucose | 180 minutes | 152.7 ± 51.6 | 102.6 ± 39.9 |

After plotting the concentration of blood glucose level over time of treated verses non-treated groups, the area under each curve was calculated to determine the glucose exposure of the treated groups of mice over time. A Student's t test with a p value of <0.001 was performed to generate a standard deviation for the average calculated glucose exposure of the group treated with Compound 101 as compared to the group treated with vehicle alone. Data for glucose exposure are summarized below in Table IV:

TABLE IV

| Glucose Exposure (Area Under the Curve; AUC) | |
|---|---|
| VEHICLE BLOOD GLUCOSE LEVELS AUC (MG × MIN/DL) | COMPOUND 101 BLOOD GLUCOSE LEVELS AUC (MG × MIN/DL) |
| 17980.2 ± 2114.5 | 8424.7 ± 1922.5** |

**p < 0.01 Student's t-test

Based upon the data generated related to blood glucose levels measured over time and the total amount of glucose exposure over the time, the data demonstrate that Compound 101 effectively controls glucose levels in vivo. These data also demonstrate that Compound 101 can be used as an effective anti-diabetic compound.

The present invention is not to be limited in scope by the specific embodiments disclosed in the examples which are intended as illustrations of some aspects of the invention. Any embodiments which are functionally equivalent are within the scope of this invention. Various modifications of the invention will become apparent to those skilled in the art and are intended to fall within the appended claims. A number of references have been cited, the entire disclosures of which are incorporated herein by reference.

What is claimed is:
1. A compound of Formula I

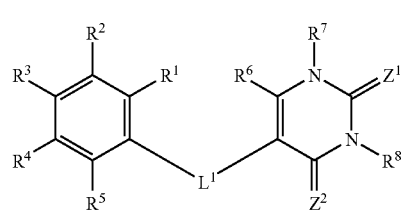

wherein:
$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^2$, $NR^{c2}S(O)_2R^{b2}$, and $S(O)_2NR^{c2}R^{d2}$;

$R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $NR^{c2}R^{d2}$, $S(O)_2R^2$, $NR^{c2}S(O)_2R^{b2}$, and $S(O)_2NR^{c2}R^{d2}$;

R⁴ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO₂, OR$^{a2}$, SRz$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁵ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

or two adjacent groups of R¹, R², R³, R⁴, and R⁵ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁶ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO₂, OR$^{a1}$, SR$^{a1}$, C(O)R$^{b1}$, C(O)NR$^{c1}$R$^{d1}$, C(O)OR$^{a1}$, OC(O)$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, or S(O)₂NR$^{c1}$R$^{d1}$, wherein each of said $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)₂R$^{b2}$, NR$^{c2}$S(O)₂R$^{b2}$, and S(O)₂NR$^{c2}$R$^{d2}$;

R⁷ is H, $C_{1-6}$alkyl, $C_{1-6}$haloalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)₂R$^{b1}$, or S(O)₂NR$^{c1}$R$^{d1}$;

R⁸ is H, $C_{1-6}$alkyl, $C_{1-6}$haloalkyl, $C_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)₂R$^{b1}$, or S(O)₂NR$^{c1}$R$^{d1}$;

R$^{a1}$, R$^{b1}$, R$^{c1}$, and R$^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO₂, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO₂, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

R$^{a2}$, R$^{b2}$, R$^{c2}$, and R$^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, NO₂, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or R$^{c2}$ and R$^{d2}$ together with the N atom to which they are attached form a 4-, 5-, 6-, or 7-membered heterocycloalkyl group or heteroaryl group, each optionally substituted with 1, 2, or 3 substituents independently selected from OH, NO₂, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

Z¹ is O, S, or NR⁹;

R⁹ is H, OH, $C_{1-6}$alkoxy, $C_{1-6}$haloalkyl, $C_{1-6}$hydroxyalkyl, aryloxy, heteroaryloxy, CN, or NO₂;

Z² is O, S, or NR¹⁰;

R¹⁰ is H, OH, $C_{1-6}$alkoxy, $C_{1-6}$haloalkyl, $C_{1-6}$hydroxyalkyl, aryloxy, heteroaryloxy, CN, or NO₂;

L¹ is O, S, or NR¹¹; and

R¹¹ is H, $C_{1-6}$alkyl, $C_{1-6}$haloalkyl, $C_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)₂R$^{b1}$, or S(O)₂NR$^{c1}$R$^{d1}$;

or a pharmaceutically acceptable salt thereof;

provided that the compound is not 5-m-methylphenoxyuracil or a pharmaceutically acceptable salt thereof.

2. The compound, or pharmaceutically effective salt thereof, of claim 1, wherein the compound of Formula I has Formula Ia:

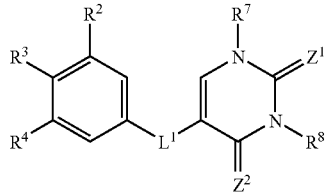

wherein:

$R^2$, $R^3$, and $R^4$ are each, independently, H, halo, $C_{1-6}$alkyl, $C_{1-6}$hydroxyalkyl, or $C_{1-6}$haloalkyl;

$R^7$ is H, $C_{1-6}$alkyl, $C(O)R^{b1}$, $C(O)NR^{c1}R^{d1}$, or $C(O)OR^{a1}$;

$R^8$ is H, $C_{1-6}$alkyl, $C(O)R^{b1}$, $C(O)NR^{c1}R^{d1}$, or $C(O)OR^{a1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O or S;

$Z^2$ is O or S; and $L^1$ is O or S.

3. A compound of Formula Ib

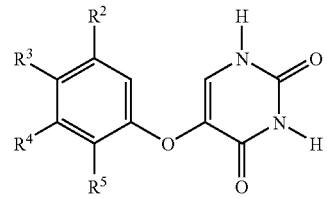

wherein:

$R^2$, $R^3$, $R^4$, and $R^5$ are each, independently, H, F, Cl, $CH_3$, $SCH_3$, $OCH_3$, $C(CH_3)_3$, $CH(CH_3)_2$, or $C_2H_5$;

or a pharmaceutically acceptable salt thereof;

provided that the compound is not 5-m-methylphenoxyuracil or a pharmaceutically acceptable salt thereof.

4. The compound of claim 1 wherein $R^1$ and $R^5$ are each, independently, H, halo, $C_{1-6}$alkyl, $C_{1-6}$hydroxyalkyl, or $C_{1-6}$haloalkyl.

5. The compound of claim 1 wherein $R^1$ and $R^5$ are each, independently, H or $C_{1-3}$alkyl.

6. The compound of claim 1 wherein $R^2$, $R^3$, and $R^4$ are each, independently, H, halo, $C_{1-6}$alkyl, $C_{1-6}$hydroxyalkyl, or $C_{1-6}$haloalkyl.

7. The compound of claim 1 wherein $R^2$, $R^3$, and $R^4$ are each, independently, H, $C_{1-6}$alkyl, $C_{1-6}$hydroxyalkyl, or $C_{1-6}$haloalkyl.

8. The compound of claim 1 wherein $R^2$, $R^3$, and $R^4$ are each, independently, H or $C_{1-6}$alkyl.

9. The compound of claim 1 wherein $R^2$, $R^3$, and $R^4$ are each, independently, H or $C_{1-3}$alkyl.

10. The compound of claim 1 wherein $R^6$ is H, halo, $C_{1-6}$alkyl, $C_{1-6}$hydroxyalkyl, or $C_{1-6}$haloalkyl.

11. The compound of claim 1 wherein $R^6$ is H or $C_{1-3}$alkyl.

12. The compound of claim 1 wherein $R^7$ is H, $C_{1-6}$alkyl, $C(O)R^{b1}$, $C(O)NR^{c1}R^{d1}$, or $C(O)OR^{a1}$.

13. The compound of claim 1 wherein $R^7$ is H.

14. The compound of claim 1 wherein $R^8$ is H, $C_{1-6}$alkyl, $C(O)R^{b1}$, $C(O)NR^{c1}R^{d1}$, or $C(O)OR^{a1}$.

15. The compound of claim 1 wherein $R^8$ is H.

16. The compound of claim 1 wherein $Z^1$ is O or S.

17. The compound of claim 1 wherein $Z^1$ is O.

18. The compound of claim 1 wherein $Z^1$ is NH, N(OH), N—O—$C_{1-6}$alkyl, N—O-phenyl, CN, or $NO_2$.

19. The compound of claim 1 wherein $Z^2$ is O or S.

20. The compound of claim 1 wherein $L^1$ is O or S.

* * * * *

UNITED STATES PATENT AND TRADEMARK OFFICE
CERTIFICATE OF CORRECTION

Page 1 of 1

PATENT NO. : 8,552,184 B2
APPLICATION NO. : 12/495857
DATED : October 8, 2013
INVENTOR(S) : Andrew G. Reaume et al.

It is certified that error appears in the above-identified patent and that said Letters Patent is hereby corrected as shown below:

In the Claims

In claim 1, column 38, line 32, please replace "$S(O)_2 R^{2}$" with -- $S(O)_2 R^{b2}$ --.

In claim 1, column 38, line 67, please replace "$S(O)_2 R^{2}$" with -- $S(O)_2 R^{b2}$ --.

In claim 1, column 39, line 14, please replace "$SRz^{a2}$" with -- $SR^{a2}$ --.

In claim 1, column 39, line 55, please replace "$OC(O)^{b1}$" with -- $OC(O)R^{b1}$ --.

Signed and Sealed this
Eighteenth Day of February, 2014

Michelle K. Lee
*Deputy Director of the United States Patent and Trademark Office*